United States Patent [19]

Haag et al.

[11] 4,279,830

[45] * Jul. 21, 1981

[54] CONVERSION OF SYNTHESIS GAS TO HYDROCARBON MIXTURES UTILIZING DUAL REACTORS

[75] Inventors: Werner O. Haag, Lawrenceville; Tracy J. Huang, Trenton, both of N.J.

[73] Assignee: Mobil Oil Corporation, New York, N.Y.

[*] Notice: The portion of the term of this patent subsequent to Jul. 3, 1996, has been disclaimed.

[21] Appl. No.: 44,872

[22] Filed: Jun. 1, 1979

Related U.S. Application Data

[63] Continuation-in-part of Ser. No. 826,487, Aug. 22, 1977, Pat. No. 4,159,995.

[51] Int. Cl.³ .............................................. C07L 1/04
[52] U.S. Cl. .................................... 518/700; 208/950; 585/407; 585/408; 585/415; 585/322; 585/324; 585/500; 518/706; 518/711; 518/721
[58] Field of Search ............... 260/449.6 R, 449.6 M, 260/449 R, 449 M, 449 L, 450; 585/407, 408, 415, 322, 324; 208/46, 120, 950

[56] References Cited

U.S. PATENT DOCUMENTS

| | | | |
|---|---|---|---|
| 2,526,934 | 10/1950 | Clark | 260/449 L |
| 2,671,103 | 3/1954 | Kolbel et al. | 260/449 S |
| 2,685,596 | 8/1954 | Buchmann | 260/449 S |
| 2,852,350 | 9/1958 | Kolbel et al. | 260/449 L |
| 4,046,829 | 9/1977 | Ireland | 260/449 R |
| 4,046,830 | 9/1977 | Kuo | 260/449 R X |
| 4,046,831 | 9/1977 | Kuo | 260/449 R X |
| 4,049,741 | 9/1977 | Kuo et al. | 260/449 R X |
| 4,086,262 | 4/1978 | Chang et al. | 260/449.6 R |
| 4,159,995 | 7/1979 | Haag et al. | 260/450 |

FOREIGN PATENT DOCUMENTS

| | | | |
|---|---|---|---|
| 709560 | 3/1954 | United Kingdom | 260/449.6 |
| 780577 | 8/1957 | United Kingdom | 260/449.6 |

OTHER PUBLICATIONS

Kolbel, Chemie Ingenuin Technik 28, No. 6, pp. 381-388, 1956.

*Primary Examiner*—Howard T. Mars
*Attorney, Agent, or Firm*—C. A. Huggett; M. G. Gilman; C. J. Speciale

[57] ABSTRACT

The conversion of less than 1 $H_2/CO$ ratio syngas to high yield of $C_3$ plus product is accomplished with a CO reducing catalyst comprising shift characteristics and the product of Fischer-Tropsch synthesis is converted to premium gasoline and distillate fuels by contact with acidic ZSM-5 zeolite.

The syngas conversion may be accomplished in any catalyst system permitting a very close temperature control on the exotherm encountered and the gasoline-distillate yield relationship may be varied as a function of temperature and pressure.

11 Claims, 1 Drawing Figure

Figure 1

CONVERSION OF SYNTHESIS GAS TO HYDROCARBON MIXTURES UTILIZING DUAL REACTORS

This application is a continuation-in-part of Ser. No. 826,487, filed Aug. 22, 1977 and now U.S. Pat. No. 4,159,995.

BACKGROUND OF THE INVENTION

1. Field of the Invention

This invention is concerned with an improved method and combination process for converting synthesis gas, i.e. mixtures of gaseous carbon oxides with hydrogen generally CO rich, to hydrocarbon mixtures.

Processes for the conversion of coal and other hydrocarbons such as natural gas to a gaseous mixture consisting essentially of hydrogen and carbon monoxide, or of hydrogen and carbon dioxide, or of hydrogen and carbon monoxide and carbon dioxide, are well known. An excellent summary of the art of gas manufacture, including synthesis gas, from solid and liquid fuels, is given in *Encyclopedia of Chemical Technology*, Edited by Kirk-Othmer, Second Edition, Volume 10, pages 353–433 (1966), Interscience Publishers, New York, N.Y., the contents of which are herein incorporated by reference. The techniques for gasification of coal or other solid, liquid or gaseous fuel are not considered to be a part of this invention.

It is well known that synthesis gas comprising carbon monoxide and hydrogen will undergo conversion to form reduction products of carbon monoxide, at temperatures in the range of 300° F. to about 850° F. and pressures in the range of one to one thousand atmospheres, over a fairly wide variety of catalysts. The Fischer-Tropsch process, for example, which has been extensively studied, produces a range of hydrocarbons, waxy materials and some liquid materials which have been used as low octane gasoline. The types of catalysts that have been studied for this and related processes include those based on metals or oxides of iron, cobalt, nickel, ruthenium, thorium, rhodium and osmium.

The range of catalysts and catalyst modifications disclosed in the art encompasses an equally wide range of conversion conditions for the reduction of carbon monoxide by hydrogen and provides considerable flexibility toward obtaining selected boiling range products. Nonetheless, in spite of this flexibility, it has not been possible heretofore to provide a catalyst for medium pressure operation (5–30 atm) which will produce particularly olefin compositions comprising primarily internal double bond characteristics and boiling in the gasoline boiling range. A review of the status of this art is given in "Carbon Monoxide-Hydrogen Reactions", *Encyclopedia of Chemical Technology*, Edited by Kirk-Othmer, Second Edition, Volume 4, pages 446–488, Interscience Publishers, New York, N.Y.

The conversion of synthesis gas to hydrocarbon mixtures is disclosed in copending application Ser. No. 583,353, filed June 2, 1975, and copending application Ser. No. 566,167, filed Apr. 4, 1975. Compositions of iron, cobalt or nickel deposited in the inner absorption regions of crystallize zeolites are described in U.S. Pat. No. 3,013,990. Attempts to convert synthesis gas over X-zeolite base exchanged with iron, cobalt and nickel are described in Erdoel und Kohle—Erdgas, Petrochemie; Brennstoff—Chemie, Volume 25, No. 4, pages 187–188, April 1972.

One particularly desirable catalyst used in the conversion of syngas has been potassium promoted iron, which has been used in combination with special types of zeolites, such as ZSM-5, in order to produce valuable hydrocarbons. Thus, for example, copending Application Ser. No. 566,167, now abandoned, is directed towards the conversion of syngas with potassium promoted iron in admixture with HZSM-5. Although the process of this copending application is indeed effective in producing products having a substantial quantity of aromatics, nevertheless there are disadvantages associated with said process, primarily in the regeneration aspect of the catalyst. It is known that when processes of this type are operated under conditions which favor the production of aromatics, there are also produced substantial amounts of coke which are deposited about the acid ZSM-5 catalyst. This requires that the catalyst be subjected to frequent regeneration, and due to the fact that the process of said copending application Ser. No. 566,167 involved a catalyst mixture containing an iron catalyst and a ZSM-5 catalyst, the extent and amount of regeneration were limited by the effect that the regeneration would have on the iron component. Thus, although HZSM-5 by itself exhibits a remarkable stability with regard to regeneration of the same by burning off carbon deposits, the same is not true with respect to a Fischer-Tropsch catalyst in general, and iron promoted potassium in particular.

In U.S. Pat. No. 4,086,262 issued Apr. 25, 1978, there is disclosed a process for the conversion of synthesis gas using a single stage process wherein the catalyst is a mixture of an iron containing Fischer-Tropsch catalyst and a ZSM-5 type zeolite. One of the examples, however, is directed towards a two bed operation wherein syngas is contacted over a first fixed catalyst bed containing an iron catalyst and the total product is thereafter contacted in a second fixed catalyst bed containing a ZSM-5 type zeolite. The example resulted in poor aromatic production and excessive methane production.

In copending Application Ser. No. 614,586, filed Sept. 18, 1975, now U.S. Pat. No. 4,046,830, issued Sept. 6, 1977, there is disclosed a process wherein the total effluent from a Fischer-Tropsch operation is upgraded over a ZSM-5 type zeolite. Although the process of said application is indeed a valuable one, it has been found that the process can be improved by operating within a more selective range of process conditions. Thus, the instant invention represents an improvement over the operation of U.S. Pat. No. 4,046,830 and copending Application Ser. No. 826,487 filed Aug. 22, 1977 and now U.S. Pat. No. 4,159,995.

SUMMARY OF THE INVENTION

It has been discovered that a highly aromatic or a highly olefinic gasoline of enhanced octane number or a gasoline plus distillate mixture can be obtained in greater yield from synthesis gas, i.e. mixtures of hydrogen gas with gaseous carbon oxide or the equivalents of such mixtures utilizing a selected synthesis gas composition of low $H_2/CO$ ratio in a relatively special Fischer-Tropsch syngas conversion operation and in a sequentially arranged dual reactor conversion process. In a first reactor of the sequence of reactors, the low $H_2/CO$ ratio ($\leq 1.0$) syngas mixture is reacted in the presence of a special Fischer-Tropsch CO reducing catalyst under severely restricted and preselected reaction conditions favoring the formation of $C_1$ to $C_{40}$ hydrocarbons and oxygenates. The product obtained from this first stage syngas conversion, all or a part thereof, is thereafter processed in a second reactor with a special crystalline zeolite catalyst such as HZSM-5 zeolite of desired acid activity (α activity <90) to yield a synthetic hydrocarbon product wherein the methane plus ethane yield is restricted to less than about 20 weight percent and the $C_5+$ hydrocarbon product fraction is at least 45 weight percent. A gasoline fraction boiling less than 400° F. at its 90% overhead is produced by the combination.

The process combination of this invention allows for considerable flexibility with respect to both reaction conditions and product produced. The different catalysts used in the separate and sequentially arranged reactors can be used under more selective conversion conditions and each catalyst so used can be regenerated separately such that the process is capable of being operated at long on-stream times. The first reactor or Fischer-Tropsch syngas conversion operation is carried out under conditions such that coke formation is restricted. The Fischer-Tropsch catalyst can be separated and regenerated or replaced with fresh catalyst. A swing reactor system, for example, may be used for this purpose. It is known by those skilled in the art that regeneration conditions for a Fischer-Tropsch catalyst, whether iron, cobalt or other suitable CO reducing Fischer-Tropsch metal, differ from those necessary for regenerating an acidic zeolite catalyst used in the combination operation.

The synthesis gas converted in the combination process of the invention may be prepared from fossil fuels by any one of the known methods, including in-situ gasification processes by the underground partial combustion of coal and petroleum deposits. The term fossil fuels, as used herein, is intended to include anthracite and bituminous coal, lignite, crude petroleum, shale oil, oil from tar sands, natural gas, as well as fuels derived from simple physical separations or more profound transformations of these materials, including coked coal, petroleum coke, gas oil, residue from petroleum distillation, coke oven gas rich in CO or any two or more of the foregoing materials in combination. Other carbonaceous fuels such as peat, wood and cellulosic waste materials also may be used.

The raw synthesis gas produced from fossil fuels will contain various materials and impurities such as particulates, sulfur, methane and metal carbonyl compounds, and will be characterized by a hydrogen-to-carbon oxides ratio which will depend on the fossil fuel and the particular gasification technology utilized. In general, it is desirable for improving the efficiency of subsequent conversion steps to purify the raw synthesis gas by the removal of impurities and provide a relatively clean mixture of hydrogen and carbon oxides. Techniques for such purification are known and are not part of this invention. However, it is preferred to adjust the formed hydrogen-to-carbon oxides volume ratio such as by the water-gas shift reaction to provide an $H_2/CO$ gas ratio in the range of from 0.5 to about 1.0 and more usually within the range of 0.6 to 0.8 for use in this invention. Should the purified synthesis gas be excessively rich in carbon monoxide, it may be brought within the preferred range by the well known water-gas shift reaction. On the other hand, should the synthesis gas be excessively rich in hydrogen, it may be adjusted into the preferred range by the addition of carbon monoxide or carbon dioxide. It is also contemplated charging water with low $H_2/CO$ ratio gas passed to the Fischer-Tropsch operation. Purified synthesis gas adjusted to contain a volume ratio of hydrogen-to-carbon monoxide within the above defined range will be referred to as adjusted synthesis gas. It is contemplated obtaining such syngas mixtures preferably by low cost syngas generation means.

The synthesis gas used in this invention includes art-recognized equivalents to the already-described mixtures of hydrogen gas with gaseous carbon oxides. Mixtures of carbon monoxide and steam, for example, or of carbon dioxide and hydrogen, to provide adjusted synthesis gas by in-situ reaction, are contemplated.

The catalysts employed in the first reactor of this invention include Fischer-Tropsch synthesis catalysts which contain (1) hydrocarbon synthesis activity and (2) activity for water-gas shift reaction. The two basic reactions accomplished with such catalysts are shown below in idealized form:

$$2H_2 + CO \rightarrow (CH_2)_n + H_2O \quad (1)$$

$$H_2O + CO \rightleftharpoons CO_2 + H_2 \quad (2)$$

where $(CH_2)_n$ stands for the hydrocarbons produced. Some Fischer-Tropsch catalysts possess activity for accomplishing both reactions, such as iron containing Fischer-Tropsch catalysts. Others catalyze essentially only the synthesis reaction of equation (1) above, such as Co or Ru. Cobalt or ruthenium catalysts can be used in the present invention when a separate shift catalyst component is added. Examples of some specific shift catalysts are Fe, Cu, Zn and Cr which may be used alone or in combination with one another to provide shift activity to, for example, cobalt and ruthenium.

When mixtures of Fischer-Tropsch synthesis and shift catalysts are used, their ratio is preferably chosen such that reaction (2) above identified occurs at an equal or greater rate than reaction (1).

In general, synthesis catalysts used in the first reactor are recognized as CO reduction catalysts and include iron, ruthenium, cobalt, rhodium, osmium and manganese. They may contain additional promoters such as alkali, alkaline earth (Group II), zinc oxide, vanadia, zirconia, copper, etc. Preferred catalysts include potassium promoted iron Fe(K) with and without copper.

Prior to syngas conversion, Fischer-Tropsch synthesis catalysts are generally reduced with hydrogen or hydrogen containing gas at a pressure from 0 psig to synthesis operating pressure. In case that a coprecipitated Fe-K or Fe-K-Cu catalyst is used, the preferred pretreatment procedure involves carbiding with low $H_2/CO$ gas or CO alone at a temperature in the range of 480° to 610° F. at a pressure up to synthesis operating pressure. The catalyst can also be pretreated by carbiding, followed by hydrogen reduction (or nitriding with $NH_3$). Alternatively, it can be pretreated by nitriding with $NH_3$ alone.

Optionally, ZSM-5 zeolites in the form of $H^+$ or $K^+$ can be admixed with a CO reduction catalyst and used as a Fischer-Tropsch synthesis catalyst.

The crystalline aluminosilicate component used in the second reactor is a special crystalline zeolite such as ZSM-5 zeolite which is characterized by a pore dimension greater than about 5 Angstroms, i.e. it is capable of sorbing paraffins, it has a silica-to-alumina ratio of at least 12 and a constraint index within the range of 1 to 12. Zeolite A, for example, with a silica-to-alumina ratio of 2.0 is not useful in this invention, and it has no pore dimension greater than about 5 Angstroms.

The crystalline aluminosilicates herein referred to, also known as zeolites, constitute an unusual class of natural and synthetic minerals. They are characterized by having a rigid crystalline framework structure composed of an assembly of silicon and aluminum atoms, each surrounded by a tetrahedron of shared oxygen atoms, and a precisely defined pore structure. Exchangeable cations are present in the pores.

The zeolites utilized herein exhibit some unusual properties. They are very active even with silica-to-alumina ratios exceeding 30. This activity is surprising, since catalytic activity of zeolites is generally attributed to framework aluminum atoms and cations associated with these aluminum atoms. These zeolites retain their crystallinity for long periods in spite of the presence of steam even at high temperatures which induce irreversible collapse of the crystal framework of other zeolites, e.g. of the X and A type. Furthermore, carbonaceous deposits, when formed, may be removed by burning at higher than usual temperatures to restore activity. In many environments the zeolites of this class exhibit very low coke forming capability, conducive to very long times on stream between burning regenerations.

An important characteristic of the crystal structure of this class of zeolites is that it provides constrained access to, and egress from, the intracrystalline free space by virtue of having a pore dimension greater than about 5 Angstroms and pore windows of about a size such as would be provided by 10-membered rings of oxygen atoms. It is to be understood, of course, that these rings are those formed by the regular disposition of the tetrahedra making up the anionic framework of the crystalline aluminosilicate, the oxygen atoms themselves being bonded to the silicon or aluminum atoms at the centers of the tetrahedra. Briefly, the preferred zeolites useful in this invention have a silica-to-alumina ratio of at least about 12 and a structure providing constrained access to the crystalline free space.

The silica-to-alumina ratio referred to may be determined by conventional analysis. This ratio is meant to represent, as closely as possible, the ratio in the rigid anionic framework of the zeolite crystal and to exclude aluminum in the binder or in cationic or other form within the channels. Although zeolites with a silica-to-alumina ratio of at least 12 are useful, it is preferred to use zeolites having higher ratios of at least about 30. Such zeolites, after activation, acquire an intracrystalline sorption capacity for normal hexane which is greater than that for water, i.e., they exhibit "hydrophobic" properties. It is believed that this hydrophobic character is advantageous in the present invention.

The zeolites useful as catalysts in this invention freely sorb normal hexane and have a pore dimension greater than about 5 Angtroms. In addition, their structure must provide constrained access to some larger molecules. It is sometimes possible to judge from a known crystal structure whether such constrained access exists. For example, if the only pore windows in a crystal are formed by 8-membered rings of oxygen atoms, then access by molecules of larger cross-section than normal hexane is substantially excluded and the zeolite is not of the desired type. Zeolites with windows of 10-membered rings are preferred, although excessive puckering or pore blockage may render these zeolites substantially ineffective. Zeolites with windows of 12-membered rings do not generally appear to offer sufficient constraint to produce the advantageous conversions desired in the instant invention, although structures can be conceived, due to pore blockage or other cause, that may be operative.

Rather than attempt to judge from crystal structure whether or not a zeolite possesses the necessary constrained access, a simple determination of the "constraint index" may be made by continuously passing a mixture of equal weight of normal hexane and 3-methylpentane over a small sample, approximately 1 gram or less, of zeolite at atmospheric pressure according to the following procedure. A sample of the zeolite, in the form of pellets or extrudate, is crushed to a particle size about that of coarse sand and mounted in a glass tube. Prior to testing, the zeolite is treated with a stream of air at 1000° F. for at least 15 minutes. The zeolite is then flushed with helium and the temperature adjusted between 550° F. and 950° F. to give an overall conversion between 10% and 60%. The mixture of hydrocarbons is passed at 1 liquid hourly space velocity (i.e., 1 volume of liquid hydrocarbon per volume of catalyst per hour) over the zeolite with a helium dilution to give a helium to total hydrocarbon mole ratio of 4:1. After 20 minutes on stream, a sample of the effluent is taken and analyzed, most conveniently by gas chromatography, to determine the fraction remaining unchanged for each of the two hydrocarbons.

The "constraint index" is calculated as follows:

$$\text{Constraint Index} = \frac{\log_{10} (\text{fraction of n-hexane remaining})}{\log_{10} (\text{fraction of 3-methylpentane remaining})}$$

The constraint index approximates the ratio of the cracking rate constants for the two hydrocarbons. Catalysts suitable for the present invention are those which employ a zeolite having a constraint index from 1.0 to 12.0. Constraint Index (C.I.) values for some typical zeolites, including some not within the scope of this invention, are:

| CAS | C.I. |
|---|---|
| Erionite | 38 |
| ZSM-5 | 8.3 |
| ZSM-11 | 8.7 |
| ZSM-35 | 6.0 |
| TMA Offretite | 3.7 |
| ZSM-38 | 2.0 |
| ZSM-12 | 2 |
| Beta | 0.6 |
| ZSM-4 | 0.5 |
| Acid Mordenite | 0.5 |
| REY | 0.4 |
| Amorphous Silica-alumina | 0.6 |

The above-described Constraint Index is an important, and even critical, definition of those zeolites which are useful to catalyze the instant process. The very nature of this parameter and the recited technique by which it is determined, however, admit of the possibility that a given zeolite can be tested under somewhat different conditions and thereby have different constraint indexes. Constraint Index seems to vary somewhat with severity of operation (conversion). Therefore, it will be appreciated that it may be possible to so select test conditions to establish multiple constraint indexes for a particular given zeolite which may be both inside and outside the above defined range of 1 to 12.

Thus, it should be understood that the parameter and property "Constraint Index" as such value is used herein is an inclusive rather than an exclusive value.

That is, a zeolite when tested by any combination of conditions within the testing definition set forth hereinabove to have a constraint index of 1 to 12 is intended to be included in the instant catalyst definition regardless that the same identical zeolite tested under other defined conditions may give a constraint index value outside of 1 to 12.

The class of zeolites defined herein is exemplified by ZSM-5, ZSM-11, ZSM-12, ZSM-21, and other similar materials. Recently issued U.S. Pat. No. 3,702,886 describing and claiming ZSM-5 is incorporated herein by reference.

ZSM-11 is more particularly described in U.S. Pat. No. 3,709,979, the entire contents of which are incorporated herein by reference.

ZSM-12 is more particularly described in U.S. Pat. No. 3,832,449, the entire contents of which are incorporated herein by reference.

U.S. application Ser. No. 358,192, filed May 7, 1973, the entire contents of which are incorporated herein by reference, describes a zeolite composition, and a method of making such, designated as ZSM-21 which is useful in this invention. Recent evidence has been adduced which suggests that this composition may be composed of at least two (2) different zeolites, designated ZSM-35 and ZSM-38, one or both of which are the effective material insofar as the catalysis of this invention is concerned. Either or all of these zeolites is considered to be within the scope of this invention. ZSM-35 is described in U.S. application Ser. No. 528,061, filed Nov. 29, 1974. ZSM-38 is described in U.S. application Ser. No. 528,060, filed Dec. 29, 1974.

The specific zeolites described, when prepared in the presence of organic cations, are substantially catalytically inactive, possibly because the intracrystalline free space is occupied by organic cations from the forming solution. They may be activated by heating in an inert atmosphere at 1000° F. for 1 hour, for example, followed by base exchange with ammonium salts, followed by calcination at 1000° F. in air. The presence of organic cations in the forming solution may not be absolutely essential to the formation of this special type zeolite; however, the presence of these cations does appear to favor the formation of this special type of zeolite. More generally, it is desirable to activate this type zeolite by base exchange with ammonium salts, followed by calcination in air at about 1000° F. for from about 15 minutes to about 24 hours.

Natural zeolites may sometimes be converted to this type zeolite by various activation procedures and other treatments such as base exchange, steaming, alumina extraction and calcination, alone or in combinations. Natural minerals which may be so treated include ferrierite, brewsterite, stilbite, dachiardite, epistilbite, heulandite and clinoptilolite. The preferred crystalline aluminosilicates are ZSM-5, ZSM-11, ZSM-12 and ZSM-21, with ZSM-5 in the acid form, i.e. H-ZSM-5, being particularly preferred.

In a preferred aspect of this invention, the initial zeolites useful as catalysts herein are selected as those having a crystal framework density, in the dry hydrogen form, of not substantially below about 1.6 grams per cubic centimeter. It has been found that zeolites which satisfy all three of these requirements are most desired. Therefore, the preferred catalysts of this invention are those comprising zeolites having a constraint index as defined above of about 1 to 12, a silica-to-alumina ratio of at least about 12 and a dried crystal density of not substantially less than about 1.6 grams per cubic centimeter. The dry density for known structures may be calculated from the number of silicon plus aluminum atoms per 1000 cubic Angstroms, as given e.g. on page 19 of the article on "Zeolite Structure" by W. M. Meier. This paper, the entire contents of which are incorporated herein by reference, is included in "Proceedings of the Conference on Molecular Sieves, London, April 1967", published by the Society of Chemical Industry, London, 1968. When the crystal structure is unknown, the crystal framework density may be determined by classical pycnometer techniques. For example, it may be determined by immersing the dry hydrogen form of the zeolite in an organic solvent which is not sorbed by the crystal. It is possible that the unusual sustained activity and stability of this class of zeolites are associated with its high crystal anionic framework density of not less than about 1.6 grams per cubic centimeter. This high density of course must be associated with a relatively small amount of free space within the crystal, which might be expected to result in more stable structures. This free space, however, seems to be important as the locus of the catalytic activity.

Crystal framework densities of some typical zeolites, including some which are not within the purview of this invention, are:

| Zeolite | Void Volume | Framework Density |
| --- | --- | --- |
| Ferrierite | 0.28 cc/cc | 1.76 g/cc |
| Mordenite | .28 | 1.7 |
| ZSM-5, -11 | .29 | 1.79 |
| Dachiardite | .32 | 1.72 |
| L | .32 | 1.61 |
| Clinoptilolite | .34 | 1.71 |
| Laumontite | .34 | 1.77 |
| ZSM-4 (Omega) | .38 | 1.65 |
| Heulandite | .39 | 1.69 |
| P | .41 | 1.57 |
| Offretite | .40 | 1.55 |
| Levynite | .40 | 1.54 |
| Erionite | .35 | 1.51 |
| Gmelinite | .44 | 1.46 |
| Chabazite | .47 | 1.45 |
| A | .5 | 1.3 |
| Y | .48 | 1.27 |

An importnt criticality in the improved processing combination of the invention resides in the operating conditions utilized. In the first reactor of the sequence of reactor and comprising a CO reducing component with water-gas shift activity, it is proposed to charge a syngas comprising an $H_2/CO$ ratio in the range of 0.5 to 1.0, and preferably within the range of 0.6 to 0.8, in order to achieve an overall syngas conversion of at least 70% and more preferably greater than 80%. The conversion of the syngas feed is accomplished at a temperature selected from within the range of 400° to 600° F., it being preferred to use a Fischer-Tropsch temperature selected from within the range of 420° to 580° F. An operating pressure within the range of 1 to 1500 psig and more preferably in the range of 100 to 800 psig is employed. Within the above-defined operating constraints, the syngas WHSV is adjusted to achieve conversion thereof equal to or greater than 70%, it being preferred to achieve a conversion of the syngas on a once-through basis equal to or greater than 80%.

In the second reactor stage of the combination operation and comprising the special crystalline zeolite conversion catalyst specifically identified as a ZSM-5 zeolite of desired acid activity, a temperature is selected from within the range of 530° to 850° F. and more preferably from 550° to 800° F. to achieve a product selectivity favoring gasoline or a mixture of gasoline plus distillate. These products are favored by a pressure of 100 to 400 psig. On the other hand, when it is desired to emphasize production of higher boiling distillate material, a temperature within the range of 450° to 650° F. is selected and the pressure is chosen between 400 and 800 psig. In general, the pressure in the second reactor may be equal to or below that used in the first reactor. On the other hand, when it is desired to produce a diesel type fuel, the pressure in the second zeolite catalyst stage may be higher than the first or Fischer-Tropsch reactor preferred pressure range. Within these operating constraints, the syngas product of the first (Fischer-Tropsch) reactor, all or partially, is charged to the zeolite catalyst reactor at a rate within the range of 0.2 to 30 WHSV and more usually within the range of 1 to 12 WHSV, depending on the severity of the operation desired.

To facilitate obtaining desired and selected products by the above-identified combination operation, the alpha ($\alpha$) activity of the special zeolite catalyst is maintained below about 90 and preferably below 50. Zeolite catalysts as prepared often have $\alpha$ values exceeding 150. A reduction in the zeolite activity may be obtained by steaming, increasing the Si/Al ratio during synthesis, addition of alkali, etc.

Cracking activity is obtained by a standard $\alpha$-test which is fully described in a letter to the Editor entitled "Superactive Crystalline Aluminosilicate Hydrocarbon Catalysts" by P. B. Weisz and J. N. Miale appearing in "Journal of Catalysts", Volume 4, No. 4, August 1965, pages 527-529, which is incorporated herein by reference, except that it is preferred for the zeolites contemplated herein to perform the measurement of the $\alpha$-activity at a temperature of 1000° F.

The combination operation of the invention is highly versatile for varying product selectivity and this versatility may be amplified to some considerable extent by passing all or only a portion of the product of the first stage syngas conversion operation in contact with the zeolite catalyst of the second stage operation. For example, up to about 30% of the heaviest or higher boiling portion of the first reactor Fischer-Tropsch product may be withdrawn for separate catalytic treatment from lower boiling product. The hydrocarbon and oxygenated product of Fischer-Tropsch synthesis is catalytically modified by the special zeolite catalyst herein identified under selected operating conditions. Within this operating environment, it is contemplated performing the Fischer-Tropsch syngas conversion operation with the Fischer-Tropsch catalyst suspended in a liquid medium, or maintained as a fixed catalyst bed restrained within long reaction tubes of restricted cross-sectional area and/or diameter to achieve a desired indirect heat exchange with a heat exchange fluid adjacent the reaction tubes, that is, internal or external thereto. On the other hand, the catalyst may be employed in a dispersed phase reaction zone provided with indirect heat exchange coils or as a more dense fluidized catalyst bed arrangement provided with indirect heat exchange coil means suitably arranged for the purpose of removing undesired exothermic reaction heat.

The combination operation of the invention lends itself to a variety of arrangements which can be relied upon to achieve the results desired. For example, it is contemplated employing more than one Fischer-Tropsch reactor in sequential or parallel flow arrangement or a combination thereof which will permit recovering, for example, $CO_2$ by hot carbonate wash from the products of reaction and intermediate the sequential reaction stages. In this operating combination of Fischer-Tropsch reactors, it is proposed to obtain better than 60% conversion of CO in at least the first reactor of the sequence of reactors and this may be particularly accomplished by maintaining the $H_2/CO$ ratio within the low limits herein identified.

When using the Fischer-Tropsch catalyst slurried in a liquid product of Fischer-Tropsch synthesis as a liquid phase Fischer-Tropsch operation in apparatus such as a bubble column, it is contemplated using at least two such columns in sequence or parallel flow arrangement or a combination thereof. In such liquid phase systems, a portion of the liquid medium may be withdrawn and separated from catalyst particles so that a slurry of high catalyst particle concentration can be returned to the Fischer-Tropsch reactor. The liquid product freed of catalyst fines may then be passed to the zeolite catalyst conversion stage of the operation with or without entrained oxygenates of the Fischer-Tropsch operation. On the other hand, the liquid separated from catalyst fines may be passed to a catalytic operation designed particularly to form middle distillates, diesel fuels and jet fuels.

In a particularly preferred embodiment, the processing technology of the invention is directed to processing $H_2/CO$ gas in a ratio of 0.6 to 0.8 under processing conditions providing at least 90% syngas conversion to hydrocarbon and oxygenate products which are thereafter converted with a ZSM-5 zeolite to more desirable products.

$H_2/CO$ Ratio

The $H_2/CO$ ratio of the synthesis gas or syngas employed in a Fischer-Tropsch operation may be varied over a wide range. That is, in the Fischer-Tropsch operation, the $H_2/CO$ ratio used can vary from 0.2 to 6.0 as taught by U.S. Pat. No. 4,086,262 and other sources. In a commercial Fischer-Tropsch operation now in operation, the $H_2/CO$ syngas ratio used is normally greater than about 4.

It has now been found, however, that high rates of conversion of a syngas feed can be accomplished to considerable advantage by using syngas providing an $H_2/CO$ ratio in the range of 0.5 to about 1.0. The precise stoichiometry of the Fischer-Tropsch operation is a function of the composition of the reaction products and particularly the methane content of the reaction product. For synthesis products comprising up to about 25% methane, 100% syngas conversion can be achieved with a $CO_2$ free gas of $H_2/CO$ ratio of 0.5 to 2.3, provided the Fischer-Tropsch synthesis catalyst has water-gas shift activity. However, generating synthesis gas from coal with an $H_2/CO$ ratio greater than 1 is very costly and economically not particularly attractive to the processor.

The prior art comprises several references which show that the rate of syngas conversion is greatest, the higher the $H_2/CO$ ratio gas that is used. This suggests that, at a given set of processing conditions, a high conversion of the syngas feed can be achieved only with an $H_2/CO$ ratio at the high end of the stoichiometric range, e.g. about $H_2/CO$ ratio $\simeq 2$.

Figure 1:
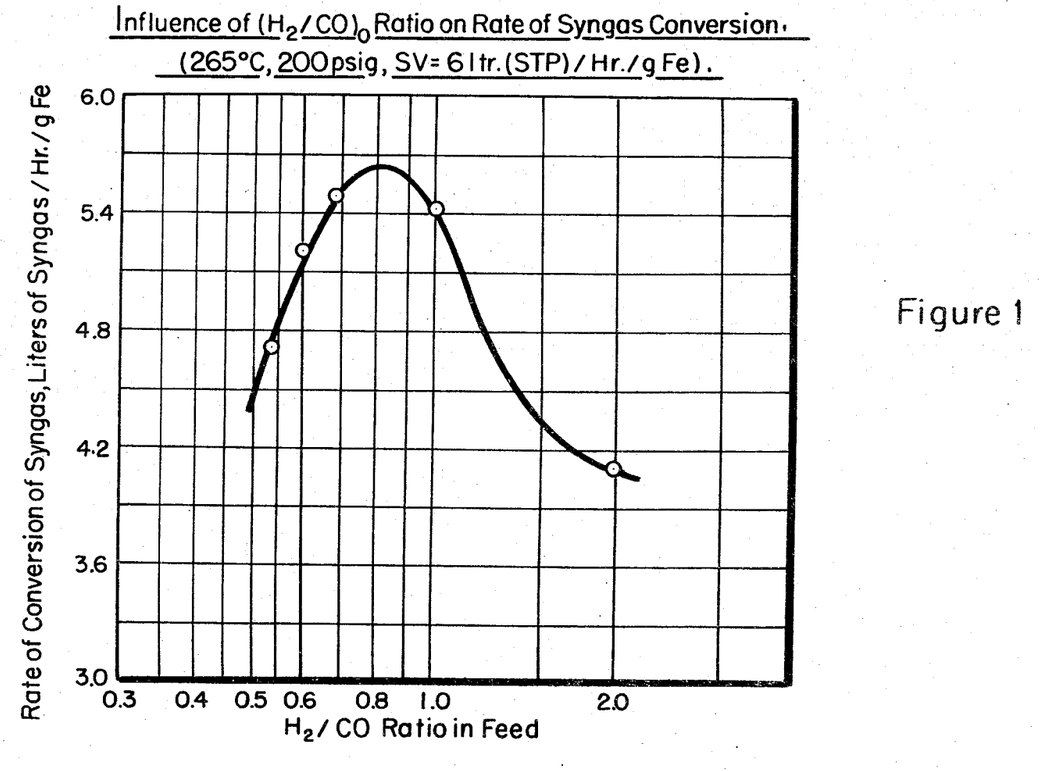

It has now been found, however, that there are some significant advantages in converting syngas providing an $H_2/CO$ ratio in the range of 0.5 to 1. That is, it has now been found quite unexpectedly that a high $H_2/CO$ ratio syngas is not essential to achieve a high rate of conversion as previously taught. On the contrary, it was found that at a high overall conversion of greater than 60% the rate of conversion of the syngas feed is especially high when processing a low $H_2/CO$ ratio syngas, with the highest conversion rate achieved with about a 0.8 $H_2/CO$ ratio gas when using a Fischer-Tropsch catalyst containing water-gas shift characteristics under selected operating conditions. This finding is clearly shown by FIG. 1. The use of a low $H_2/CO$ syngas thus has the particular advantage of allowing for high conversion per pass; and this high conversion can be achieved with a higher rate of reaction than possible with gases outside this range. Furthermore, it was found that restricting the $H_2/CO$ ratio to a value of 1 or less has a beneficial effect on the product distribution as shown in the following Table 1. The production of methane+ethane is <20% and the yield of the more valuable $C_3+$ products is at least 80%.

In addition, it was found that the yield of liquid $C_5+$ products is at least 45%.

TABLE 1

| Effect of $H_2/CO$). Ratio of Product Selectivity (265° C., 200 psig, SV = 6 liters (STP)/Hr./g Fe) | | |
| --- | --- | --- |
| $H_2/CO$ | Rate of Syngas Conversion liters (STP) of syngas/Hr./g Fe | Product Selectivity $C_1 + C_2$ in H. C. |
| 0.53 | 4.7 | 9.2 |
| 0.60 | 5.2 | 11.4 |
| 0.68 | 5.5 | 16.0 |
| 1.0 | 5.4 | 17.0 |
| 2.0 | 4.1 | 30.5 |

It is known that the cost of producing a low ratio syngas of about 0.5 is significantly less than that required for producing syngas of 1 or higher $H_2/CO$ ratio. Such low ratio syngas of about 0.5 can be adjusted if desired to within the most preferred range of 0.6 to 0.8 $H_2/CO$ by an external shift reaction. Of particular interest is the realization that water can be charged with the low ratio syngas without encountering adverse effects particularly when using a water-gas shift Fischer-Tropsch catalyst.

It is recognized that the Fischer-Tropsch synthesis reactions produce $CO_2$ which may or may not be separated before passing the Fischer-Tropsch product in contact with additional Fischer-Tropsch catalyst or the zeolite conversion catalyst as herein provided. Separated $CO_2$ may be recycled to the coal gasification operation for reaction with carbon. An important aspect of the invention is the indirect temperature control generation of steam in the highly exothermic Fischer-Tropsch synthesis operation which steam source is used to supply a substantial portion of the heat requirements of a low cost highly efficient coal gasification operation including the generation of oxygen for use in the coal gasification operation. The operating synergism between the processing steps of the combination contributes measurably to the economic and technological advance of the combination process, and such technological advance grasps from the morass of normal poor quality Fischer-Tropsch product wide spectrum carbon compounds, premium fuels by a selective conversion thereof with a special zeolite known as ZSM-5 crystalline zeolite.

In the combination operation of this invention, the Fischer-Tropsch synthesis gas conversion may be carried out in one or more reactors similar to that disclosed in the prior art. However, the special low $H_2/CO$ ratio syngas used in the present invention combination requires a special arrangement and operating care to avoid any large and/or local significant temperature increases that will lead to low selectivity for premium products, significant methane make or an undesired increased carbon deposition. Therefore, adiabatic fixed catalyst bed type flow reactors are unsuitable for the purpose. Useful reactor types are those provided with adequate heat exchange means in fixed bed catalyst reactors or fluid catalyst bed reactors. Reactor arrangements of particular advantage are those comprising suspended Fischer-Tropsch catalyst particles in a liquid medium and broadly referred to as liquid phase-catalyst reactor systems that provide excellent temperature control with the catalyst suspending liquid medium. On the other hand, elongated tubes of restricted diameter filled with fixed or suspended catalyst and surrounded by a liquid may be employed.

Especially preferred is a liquid phase bubble column reactor arrangement with suspended finely divided catalyst particles in a liquid medium such as hydrocarbon product medium. The catalyst particles suspended in the liquid medium are preferably iron particles with or without alkali promoter such as potassium of small particle size up to about 100 microns and preferably less than 40 microns. The alkali promoter is desirable to inhibit methane make.

The liquid suspending medium desirably will possess enough thermal stability to be stable under the reaction conditions employed. Therefore it is desirable to employ a high boiling portion of the reaction product. Other examples are anthracene oil, heavy petroleum fractions and silicon oil. Preferred are synthetic hydrocarbons such as the heavier fraction produced in the Fischer-Tropsch synthesis reaction. A synthetic hydrocarbon oligomer, for example the trimer, tetramer or pentamer of 1-decene, preferably after hydrogenation, may also be employed as the suspending liquid medium.

The pressure utilized in the second or zeolite catalyst conversion reactor will be, in general, equal to, higher or less than the pressure used in the first reactor, i.e., from atmospheric to about 800 psig. The space velocity in the second reactor will vary from 0.2 to 30 WHSV and more preferably from 1 to 12 WHSV. The second reactor temperature is from about 530° F. up to about 850° F. and more preferably from 550° F. to 800° F. In general, operating temperatures in the range of from about 530° F. to 650° F. favor the formation of olefinic gasoline, whereas temperatures from about 600° F. to 800° F. favor the production of aromatic gasolines, i.e. greater than 25 weight percent aromatics in the $C_5+$ fraction.

In general, the products of the present invention are considered premium fuels. Their composition can be regulated by the composition of the charge and operating conditions of the zeolite catalyst second stage operation. In one embodiment, a most desired product is a gasoline of relatively high octane number of at least about 85 research clear. Conditions to produce gasoline of either high olefin or high aromatic contents are identified herein.

It has also been found that it is possible to coproduce by two separate catalyst stages of this invention a distillate fraction—in addition to a relatively high octane gasoline of at least 80 research clear—which distillate has a very low pour point generally below 0° F. This is in contrast to a heavy waxy hydrocarbon fraction (pour point >70° F.) produced by the Fischer-Tropsch reaction itself in the absence of the second state ZSM-5 zeolite catalyst operation. The distillate material recovered from the zeolite conversion operation, generlly boiling above gasoline, may initially boil about 320° F. and is suitable for use as a diesel fuel or for jet fuel production. For example, the distillate recovered may be a 350°-570° F. fraction which has an API gravity of about 59, a cetane number of about 80 and a pour point of about −40° F. The operating conditions used in the zeolite catalyst conversion stage that favor the coproduction of gasoline and distillate fuels differ somewhat from those used for maximizing gasoline production and will vary with zeolite catalyst activity. They generlly include the use of a lower temperature and/or a higher pressure for increasing distillate yield. Distillate is intended to refer to material higher boiling than gasoline.

A temperature within the range of 450°-650° F. may be used in the second zeolite conversion stage for coproduction of gasoline and distillate at a pressure in the range of 300-1500 psig.

The second stage or zeolite catalyst conversion operation is an exothermic type of operation requiring relatively moderate temperature control means, whereas the first stage or Fischer-Tropsch catalyst conversion operation is a highly exothermic conversion operation requiring much more elaborate temperature control means. The reactions contemplated must occur in relatively close temperature control environments particularly for the Fischer-Tropsch operation in order to realize the desired conversion products of the operation. The second stage exothermic operation of the combination may be accomplished in either a fixed or fluid bed of catalyst provided with adequate indirect heat exchange means. The highly exothermic first stage Fischer-Tropsch catalyst operation, because it is processing syngas $H_2/CO$ ratio of 1 or less, and as low as 0.5 or 0.8 $H_2/CO$ ratio gas, requires a very close temperature control reaction system. Systems which may be used for this purpose not necessarily with equal success include (1) a fixed bed of catalyst in a limited diameter tube and shell reactor arrangement with indirect heat exchange fluid on the opposite side of the tube from the catalyst, (2) a limited movement bed of catalyst particles in direct contact with circulating oil and provided with external heat exchange means, (3) random movement of fine catalyst particles suspended in a liquid phase medium such as a bubble column and provided with internal, external heat exchange means or a combination thereof, and (4) a fluid bed catalyst phase operation provided with internal heat exchange means suitable for retaining the exothermic temperature of the operation within relatively narrow prescribed limits.

The preferred two stage operation of the invention comprises the use of a bubble column type of reaction system containing suspended finely divided catalyst particles in a liquid product medium of Fischer-Tropsch synthesis and maintaining close desired temperature control on the highly exothermic Fischer-Tropsch operation with the catalyst suspending liquid medium when particularly processing syngas of an $H_2/CO$ ratio in the range of 0.5 up to about 1.0. It is preferred, however, as herein identified, to maintain the $H_2/CO$ ratio from about 0.6 to about 0.8 so as to achieve high rates of conversion within relatively economic processing conditions. This bubble column with suspended Fischer-Tropsch catalyst in a liquid medium is most appropriate for achieving restricted temperature variations about any given catalyst particle and such a temperature restriction is necessary to severely limit coke deposition. Severely limiting temperature excursions in the Fischer-Tropsch operation is particularly desirable during operations selected to maximize gasoline production because of the higher temperature requirements.

The second stage of the combination operation comprising the special zeolite conversion catalyst herein identified used in a fixed or fluid bed of catalyst is relied upon to convert a highly olefinic product of the first stage with or without Fischer-Tropsch formed oxygenates under exothermic reaction conditions suitably temperature restricted to produce the desired product slate herein identified. In this zeolite catalyst conversion operation, it is contemplated using the special zeolite catalyst with an $\alpha$ (alpha) activity as high as about 90, it being more usually about 70 and preferably not above about $50\alpha$ activity.

In the two-stage syngas conversion, the product from the ZSM-5 reactor can be further upgraded by special downstream processing. For example, gasoline production can be maximized by alkylating isobutane with light olefins and polymerizing excess olefins (if any) by catalytic polymerization or olefination or dimerization. Ethylene, possibly propylene, can be recovered for chemical use. In addition, $C_2=-C_4=$ olefins can be utilized for production of middle distillate by processing over ZSM-5 zeolites at low temperature (450° to 650° F.) and high pressure (300 to 1500 psig).

EXAMPLE 1

The following example will illustrate the criticality of temperature in carrying out the novel process of this invention. Example 1a is an experiment within the operating parameters of this invention and Example 1b is the operation disclosed in Belgian Pat. No. 828,228. In each case the feed was a mixture of hydrogen and carbon monoxide having an $H_2/CO$ ratio of 1.0, the first reactor catalyst was Fe(K) and the second reactor catalyst was HZSM-5. Specific operating conditions and the results obtained are set forth in the following table.

TABLE 2

| Example No. | | 1a | 1b |
|---|---|---|---|
| Temp. (Avg.), | First Reactor | 518° F. | 700° F. |
| | Second Reactor | 650° F. | 700° F. |
| WHSV, | First Reactor | 1.0 | 1.0 |
| | Second Reactor | 1.8 | 1.4 |
| Pressure, psig | | 400 | 250 |
| Conversion, wt % | Feed | | |
| CO | 1.0 | 71 | 96.9 |
| $H_2$ | 1.0 | 70 | 76.9 |
| Syngas | | 70.5 | 86.9 |
| Wt % Hydrocarbon in Total Effluent | | 18.1 | 25.6 |
| Hydrocarbon Distribution, wt % | | | |
| $C_1 + C_2$ | | 11.7 | 61.6 |
| $C_3 + C_4$ | | 45.8 | 29.6 |
| $C_5+$ | | 42.5 | 8.8 |
| Aromatics in $C_5+$, wt % | | 61.9 | 2.3 |
| Octane No. (R + O) of Liquid Product | | 105.8 | |
| Boiling Range of Liquid Product | | | |
| 90% cut | | 387° F. | |

The above example clearly demonstrates superior results which are obtained when operating within the critical parameters of the instant invention. Thus, Example 1a resulted in the production of a hydrocarbon product wherein the $C_5+$ fraction was greater than 40 weight percent and wherein the methane plus ethane make was less than 20 weight percent. As can be seen from the results obtained in accordance with Example 1b, the methane and ethane produced was excessive and the $C_5+$ yield was only 8.8 weight percent.

EXAMPLES 2-4

In each of these examples, a mixture of hydrogen, carbon monoxide and carbon dioxide in a ratio of 4.6 to 1 to 1.6 was used as the feed and in each example the catalyst in the first reactor was Fe(K) and that in the second reactor was HZSM-5. A pressure of 400 psig was used in all examples in both the first and second reactor.

Other operating conditions, as well as the results obtained, are shown in the following table:

TABLE 3

| Example No. | | 2 | 3 | 4 |
|---|---|---|---|---|
| Temp. (Avg.), | First Reactor | 700° F. | 600° F. | 648° F. |
| | Second Reactor | 700° F. | 600° F. | 804° F. |
| WHSV, | First Reactor | 0.95 | 0.95 | 0.9 |
| | Second Reactor | 9.80 | 9.80 | 9.8 |
| Conversion, wt % | | | | |
| CO | | 91.4 | 69.3 | 66.9 |
| $H_2$ | | 34.9 | 36.2 | 38.0 |
| $CO_2$ | | 25.1 | 1.7 | −0.3 |
| Syngas | | 68.7 | 49.7 | 48.0 |
| Total Effluent wt % | | | | |
| Hydrocarbon | | 20.4 | 8.3 | 7.7 |
| $H_2$ | | 5.6 | 5.4 | 5.2 |
| CO | | 2.3 | 8.0 | 8.7 |
| $CO_2$ | | 48.6 | 64.4 | 65.6 |
| $H_2O$ | | 23.2 | 13.9 | 12.7 |
| Hydrocarbon Distribution, wt % | | | | |
| $C_1$ | | 30.9 | 12.1 | 13.3 |
| $C_2$ | | 5.5 | 1.9 | 3.4 |
| $C_2=$ | | — | 2.8 | 7.3 |
| $C_3$ | | 5.3 | 4.0 | 6.1 |
| $C_3=$ | | 0.9 | 2.9 | 9.8 |
| $i-C_4$ | | 7.4 | 2.3 | 4.8 |
| $n-C_4$ | | 4.8 | 2.6 | 3.8 |
| $C_4=$ | | 1.0 | 5.0 | 9.7 |
| $i-C_5$ | | 4.9 | 2.5 | 3.6 |
| $n-C_5$ | | 2.5 | 2.0 | 2.1 |
| $C_6+$ non-arom. | | 12.7 | 45.0 | 17.9 |
| Aromatics | | 24.1 | 16.9 | 18.3 |
| $C_1 + C_2$ in H.C., wt % | | 36.4 | 16.8 | 16.7 |
| $C_3 + C_4$ in H.C., wt % | | 19.4 | 16.8* | 31.5* |
| $C_5+$ in H.C., wt % | | 44.2 | 66.4 | 41.8 |
| Aromatics in $C_5+$, wt % | | 45.4 | 25.5 | 43.6 |

*Including $C_2=$

From the above table, it can be seen that Example 2 resulted in the production of an excessive amount of methane plus ethane, i.e., 36.4 weight percent, whereas the operations of Examples 3 and 4 resulted in acceptable methane plus ethane make while still yielding a $C_5+$ fraction of at least 40 weight percent, based on the hydrocarbons made.

The operation of Example 4 was carried out for 25 continuous days without regeneration of catalyst in either first or second reactor, thereby demonstrating catalyst stability. Although reaction conditions varied during the 25 days, the conditions set forth in the above table for Example 4 were achieved at least by the 24th day.

EXAMPLES 5-8

In each of these examples, the feed utilized was a mixture of hydrogen, carbon monoxide in a ratio of 2:1 and the pressure in both the first and second reactors was 400 psig. The first reactor in all cases contained Fe(K) and the second reactor contained HZSM-5.

Other operating parameters and the results obtained are shown in the following table.

TABLE 4

| Example No. | | 5 | 6 | 7 | 8 |
|---|---|---|---|---|---|
| Temp.(Avg.), | First Reactor | 520° F. | 520° F. | 520° F. | 520° F. |
| | Second Reactor | 520° F. | 550° F. | 650° F. | 850° F. |
| WHSV, | First Reactor | 0.7 | | | 0.4 |
| | Second Reactor | 1.2 | | | 0.8 |
| Conversion, wt % | | | | | |
| CO | | 66.4 | 77.6 | 79.4 | 94.8 |
| $H_2$ | | 29.3 | 39.6 | 42.0 | 66.7 |
| Syngas | | 54.0 | 64.9 | 66.9 | 85.4 |
| Total Effluent. wt % | | | | | |
| Hydrocarbon | | 18.2 | 20.6 | 21.8 | 26.2 |
| $H_2$ | | 9.6 | 8.2 | 7.8 | 4.5 |
| CO | | 29.1 | 19.4 | 17.9 | 4.5 |
| $CO_2$ | | 31.2 | 37.8 | 37.9 | 30.1 |
| $H_2O$ | | 11.9 | 14.1 | 14.7 | 34.6 |
| Hydrocarbon Distribution, wt % | | | | | |
| $C_1$ | | 14.9 | 11.6 | 11.4 | 17.3 |
| $C_2$ | | 6.1 | 3.7 | 4.2 | 7.4 |
| $C_2=$ | | 10.4 | — | — | — |
| $C_3$ | | 2.5 | 3.7 | 10.5 | 18.0 |
| $C_3=$ | | 5.1 | 0.9 | — | 0.1 |
| $i-C_4$ | | 0.3 | 2.7 | 12.8 | 10.7 |
| $n-C_4$ | | 2.8 | 5.8 | 9.1 | 6.9 |
| $C_4=$ | | 3.0 | 2.1 | — | — |
| $i-C_5$ | | 1.7 | 3.2 | 9.6 | 5.2 |
| $n-C_5$ | | 1.4 | 4.4 | 5.0 | 1.4 |
| $C_6+$ non-arom. | | 51.9 | 46.8 | 14.0 | 2.9 |
| Aromatics | | | 15.2 | 23.5 | 30.1 |
| $C_1 + C_2$ in H.C., wt % | | 21.0 | 15.3 | 15.6 | 24.7 |
| $C_3 + C_4$ in H.C., wt % | | 24.0* | 15.2 | 32.3 | 35.7 |
| $C_5+$ in H.C., wt % | | 55.0 | 69.6 | 52.0 | 39.6 |
| Aromatics in $C_5+$, wt % | | — | 21.8 | 45.1 | 76.0 |
| Boiling Range of Liquid Product 90% cut, °F. | | 427 | 381 | 344 | 365 |

*Including $C_2=$

As can be seen, operations in accordance with Example 5 did not produce a desired product, since the boiling range of the material was 427° to 90% overhead. As can be seen, the second reactor temperature of Example 5 was 520° F. which is outside the scope of the instant invention. Examples 6 and 7 did produce very excellent results, as can be seen from the data listed in the above table.

EXAMPLES 9-13

The procedure of Examples 5-8 was repeated, with the exception that the HZSM-5 zeolite used in the second reactor had an α-value of 16. The α-value of the HZSM-5 utilized in Examples 5-8 was 200.

The α-value is a measure of the hexane cracking activity of the catalyst and is to be determined in accordance with the method set forth by P. B. Weisz and J. N. Miale in "Journal of Catalysis", Vol. 4, No. 4, August 1965, pages 527-529, which description is herein incorporated by reference; except that the temperature of the α-measurement is 1000° F. Lower α-values than about 200 were obtained by steam treating the catalyst at elevated temperature.

Specific operating conditions as well as the results obtained are shown in the following tables.

TABLE 5

| Example No. | | 9 | 10 | 11 | 12 | 13 |
|---|---|---|---|---|---|---|
| Temp. (Avg.), °F. | First Reactor | 520 | 520 | 520 | 530 | 600 |
| | Second Reactor | 550 | 590 | 620 | 650 | 650 |
| WHSV, | First Reactor | 0.7 | | | | |
| | Second Reactor | 1.3 | | | | |
| Conversion, wt % | | | | | | |
| CO | | 77.9 | 76.8 | 79.1 | 81.6 | 93.2 |
| $H_2$ | | 32.6 | 21.0 | 29.9 | 31.5 | 51.0 |
| Syngas | | 62.8 | 58.2 | 62.7 | 64.9 | 79.1 |
| Total Effluent, wt % | | | | | | |
| Hydrocarbon | | 17.8 | 20.5 | 20.1 | 21.0 | 25.0 |
| $H_2$ | | 8.3 | 9.7 | 8.6 | 8.4 | 5.9 |
| CO | | 19.4 | 20.3 | 18.3 | 16.2 | 6.0 |
| $CO_2$ | | 42.4 | 36.7 | 40.8 | 42.8 | 49.1 |
| $H_2O$ | | 12.2 | 12.8 | 12.2 | 11.6 | 14.0 |
| Hydrocarbon Distribution, wt % | | | | | | |
| $C_1$ | | 14.0 | 14.1 | 12.0 | 13.2 | 13.2 |
| $C_2$ | | 3.6 | 4.1 | 4.0 | 4.6 | 3.9 |
| $C_2=$ | | 4.2 | 3.5 | 2.3 | — | — |
| $C_3$ | | 3.0 | 3.0 | 3.2 | 5.6 | 7.4 |
| $C_3=$ | | 7.6 | 2.9 | 2.0 | 0.9 | 1.2 |
| $i-C_4$ | | 0.4 | 1.0 | 2.9 | 8.4 | 6.3 |
| $n-C_4$ | | 3.2 | 3.1 | 4.0 | 6.3 | 4.9 |
| $C_4=$ | | 4.2 | 7.4 | 5.8 | 1.1 | 1.5 |
| $i-C_5$ | | 1.4 | 1.6 | 3.3 | 6.8 | 5.3 |
| $n-C_5$ | | 1.4 | 1.9 | 3.1 | 5.0 | 3.7 |
| $C_6+$ non-arom. | | 57.2 | 57.5 | 57.9 | 32.0 | 35.9 |
| Aromatics | | | | 5.4 | 16.1 | 16.8 |
| $C_1 + C_2$ in H.C., wt % | | 17.6 | 18.2 | 16.0 | 17.8 | 17.1 |
| $C_3 + C_4$ in H.C., wt % | | 22.5* | 20.9* | 20.3* | 22.3 | 21.2 |
| $C_5+$ in H.C., wt % | | 59.9 | 60.9 | 63.7 | 59.9 | 61.7 |
| Aromatics in $C_5+$, wt % | | — | — | 8.5 | 26.8 | 27.3 |
| Octane No. (R + O) of Liquid Product | | 90.0 | 86.9 | 86.9 | 84.7 | 87.1 |
| Boiling Range of Liquid Product 90% cut, °F. | | 398 | 383 | 361 | 358 | 359 |

*Including $C_2=$

As will be seen, operations in accordance with Examples 9–13 resulted in the production of a desired product in excellent yields with very acceptable methane plus ethane make.

Examples 9, 10, 11, 12 and 13 were run continuously for 4, 7, 8, 21 and 38 days respectively. Operating conditions may have varied for each example, but the conditions set forth in the above table were achieved at least by the last day.

EXAMPLES 14–18

The procedure of Examples 2–4 was repeated, with the exception that the HZSM-5 had an alpha value of about 66.

The results are shown below:

TABLE 6

| Example No. | | 14 | 15 | 16 | 17 | 18 |
|---|---|---|---|---|---|---|
| Temp. (Avg.), °F. | First Reactor | 600 | 600 | 626 | 644 | 648 |
| | Second Reactor | 580 | 600 | 644 | 739 | 804 |
| WHSV, | First Reactor | 1.0 | | | | |
| | Second Reactor | 9.9 | | | | |
| Conversion, wt % | | | | | | |
| CO | | 68.9 | 69.3 | 70.6 | 65.3 | 66.9 |
| $H_2$ | | 34.8 | 36.2 | 38.7 | 37.9 | 38.0 |
| $CO_2$ | | 0.4 | 1.7 | −3.5 | −1.8 | −0.3 |
| Syngas | | 48.9 | 49.7 | 50.5 | 47.0 | 48.0 |
| Total Effluent, wt % | | | | | | |
| Hydrocarbon | | 7.7 | 8.3 | 7.0 | 7.1 | 7.7 |
| $H_2$ | | 5.5 | 5.4 | 5.2 | 5.2 | 5.2 |
| CO | | 8.1 | 8.0 | 7.7 | 9.1 | 8.7 |
| $CO_2$ | | 65.2 | 64.4 | 67.7 | 66.6 | 65.6 |
| $H_2O$ | | 13.4 | 13.9 | 12.4 | 12.1 | 12.8 |
| Hydrocarbon Distribution, wt % | | | | | | |
| $C_1$ | | 12.1 | 12.1 | 12.1 | 13.6 | 13.3 |
| $C_2$ | | 2.5 | 1.9 | 2.3 | 2.6 | 3.4 |
| $C_2=$ | | 5.0 | 2.8 | 4.0 | 6.1 | 7.3 |
| $C_3$ | | 2.7 | 4.0 | 1.9 | 2.1 | 6.1 |
| $C_3=$ | | 3.0 | 2.9 | 4.1 | 9.2 | 9.8 |
| $i-C_4$ | | 2.3 | 2.3 | 2.7 | 2.1 | 4.8 |
| $n-C_4$ | | 3.0 | 2.6 | 2.3 | 2.3 | 3.8 |
| $C_4=$ | | 6.9 | 5.0 | 8.5 | 14.5 | 9.7 |
| $i-C_5$ | | 1.3 | 2.5 | 2.7 | 1.1 | 3.6 |
| $n-C_5$ | | 1.0 | 2.0 | 0.6 | 0.7 | 2.1 |
| $C_6+$ non-arom. | | 48.6 | 45.0 | 41.5 | 30.6 | 17.9 |
| Aromatics | | 11.6 | 16.9 | 17.5 | 15.0 | 18.3 |
| $C_1 + C_2$ in H.C., wt % | | 14.6 | 14.0 | 14.3 | 16.2 | 16.7 |
| $C_3 + C_4$ in H.C., wt % | | 23.9* | 19.6* | 23.5* | 36.3* | 31.5* |
| $C_5+$ in H.C., wt % | | 62.5 | 66.4 | 62.2 | 47.5 | 41.8 |
| Aromatics in $C_5+$, wt % | | 18.6 | 25.5 | 28.1 | 31.7 | 43.6 |
| Octane No. (R + O) of Liquid Product | | 91.0 | 90.1 | 92.1 | 93.0 | |
| Boiling Range of Liquid Product 90% cut, °F. | | | 374 | 385 | | |

*Including $C_2=$

EXAMPLES 19 AND 20

The procedure of Examples 14–18 was repeated with the following exceptions:
(a) The ratio feed of $H_2:CO:CO_2$ was 5.8:1.0:1.3.
(b) The α-value of HZSM-5 in Example 19 was 16. The α-value of HZSM-5 in Example 20 was 66.
(c) The operating conditions and results obtained are shown below.

TABLE 7

| Example No. | | 19 | 20 |
|---|---|---|---|
| Temp. (Avg.), °F. | First Reactor | 600 | 600 |
| | Second Reactor | 650 | 680 |
| WHSV, | First Reactor | 0.74 | 0.76 |
| | Second Reactor | 1.36 | 7.82 |
| Conversion, wt % | | | |
| CO | | 90.3 | 89.9 |
| $H_2$ | | 45.1 | 40.3 |
| $CO_2$ | | 3.9 | 14.0 |
| Syngas | | 70.9 | 71.6 |
| Total Effluent, wt % | | | |
| Hydrocarbon | | 13.4 | 15.6 |
| $H_2$ | | 6.7 | 7.2 |
| CO | | 2.8 | 3.0 |
| $CO_2$ | | 56.3 | 50.4 |
| $H_2O$ | | 20.8 | 23.7 |
| Hydrocarbon Distribution, wt % | | | |
| $C_1$ | | 19.3 | 14.0 |
| $C_2$ | | 5.4 | 2.8 |
| $C_2=$ | | — | — |
| $C_3$ | | 6.0 | 5.0 |
| $C_3=$ | | 0.5 | 1.1 |
| $i-C_4$ | | 9.5 | 10.6 |
| $n-C_4$ | | 5.5 | 5.7 |
| $C_4=$ | | — | 1.1 |
| $i-C_5$ | | 7.2 | 7.8 |
| $n-C_5$ | | 3.1 | 3.8 |
| $C_6+$ non-arom. | | 20.4 | 20.8 |
| Aromatics | | 23.1 | 27.2 |
| $C_1 + C_2$ in H.C., wt % | | 24.7 | 16.8 |
| $C_3 + C_4$ in H.C., wt % | | 21.5 | 23.5 |
| $C_5+$ in H.C., wt % | | 53.9 | 59.7 |
| Aromatics in $C_5+$, wt % | | 42.9 | 45.6 |
| Octane No. (R + O) of Liquid Product | | 87 | 95.0 |
| Boiling Range of Liquid Product 90% cut, °F. | | 366 | 359 |

EXAMPLE 21

In Example 21, a fixed bed catalyst operation was employed in both the first stage (Fischer-Tropsch synthesis) and the second stage (HZSM-5).

Ten grams of a co-precipitated. iron-potassium-copper catalyst (0.6 wt.% of $K_2CO_3$ and 3 wt.% of Cu based on metallic iron) were placed in the first tubular reactor, while 1 gram of steamed HZSM-5 ($\alpha=19$) was placed in the second tubular reactor. Prior to syngas conversion, the Fischer-Tropsch catalyst (Fe-K-Cu) was pretreated with syngas having an $H_2$/CO of 0.68 at 491° F. and 1 atmosphere at 400 ml/min of syngas (at 24° C. and 1 atmosphere) for 24 hours.

Two-stage syngas conversion was conducted in a downflow fashion at 200 psig using a syngas with an $H_2$/CO ratio of 0.68. The operating temperatures were 500° F. and 680° F. for the first and second reactors, respectively. The space velocity was 1.6 liters of syngas (at 24° C. and 1 atmosphere) per hour per gram of iron. The results are shown in Table 8. Total syngas conversion was 69% and methane in hydrocarbon was 5.8 wt.%. $C_5+$ was a high octane aromatic gasoline (Octane=91, R+O), as reflected by low boiling range (354° F. at 90% overhead) and aromatics content (25.2 wt.% of aromatics in $C_5+$).

EXAMPLE 22

In Examples 22, 23 and 24, the Fischer-Tropsch synthesis was conducted in a slurry liquid phase, a stirred-tank reactor, and a fixed-bed operation was used in the second reactor.

Three grams of a co-precipitated iron-potassium-copper catalyst (0.6 wt.% each of $K_2CO_3$ and Cu based on metallic iron) and 150 ml of a synthetic paraffinic oil (a lube oil base stock) were placed in a 300 ml stainless steel autoclave (the first reactor), equipped with a stirrer which was operated at 900 rpm. One gram of steamed HZSM-5 ($\alpha=70$) was placed in a fixed catalyst bed reactor (the second reactor). Then the whole system was purged with nitrogen while the temperatures were brought up to 482° F. and 673° F. for the first and second reactors, respectively. At that time, syngas with an $H_2$/CO ratio of 0.65 was fed into the first reactor at 193 ml/min (at 24° C. and 1 atmosphere) and the temperature of the first reactor was adjusted to 572° F. and held at that temperature for 1½ hours.

After the above pretreatment of the Fischer-Tropsch catalyst, the pressure was raised to 200 psig and the actual run started. The operating conditions and detailed product distribution are given in Table 8. Total syngas conversion was 79% and methane in hydrocarbon was only 6.7 wt.%. The selectivity (in hydrocarbon) and aromatics in $C_5+$ were 61.6 wt.% and 27.6 wt.% respectively. In addition, the $C_5+$ liquid product was essentially in the gasoline range (376° F. at 90% overhead). The results demonstrate that the two-stage process using a low $H_2$/CO syngas feed produces a high yield of high quality gasoline.

EXAMPLE 23

The two-stage syngas conversion was conducted in the same manner as in Example 22 under the same operating conditions except that the space velocity was reduced to 2.9 liters of syngas (at 24° C. and 1 atmosphere) per hour per gram of iron. The results are compiled in Table 8. High total syngas conversion (89%) with low methane production was obtained.

EXAMPLE 24

The procedure of Example 23 is repeated with the same pretreatment and operating conditions except that a synthesis gas with an $H_2$/CO mol ratio of 2.0 is used during conversion instead of 0.65 in Example 23. The total syngas conversion is only 68% (reduced from 89% in Example 23). The methane plus ethane yield is increased to 27% (from 14.7% in Example 23) and the $C_3+$ selectivity decreased to 69.5% (from 85% in Example 23).

TABLE 8

| Two-Stage Syngas Conversion at 200 psig | | Ex. 21 | Ex. 22 | Ex. 23 |
|---|---|---|---|---|
| $H_2$/CO | | 0.68 | 0.65 | 0.65 |
| Temp., | First Reactor | 500° F. | 509° F. | 509° F. |
| | Second Reactor | 680° F. | 673° F. | 672° F. |
| WHSV, | First Reactor | 0.8 | 2.8 | 1.4 |
| | Second Reactor | 7.7 | 8.5 | 4.2 |
| GHSV | First Reactor, 1/hr/g Fe | 1.6 | 5.8 | 2.9 |
| Conversion, wt. % | | | | |
| CO | | 79 | 78 | 91 |
| $H_2$ | | 56 | 80 | 87 |
| Total Syngas | | 69 | 79 | 89 |
| Total Effluent, wt. % | | | | |
| Hydrocarbon | | 18.8 | 17.0 | 19.5 |
| $H_2$ | | 2.1 | 1.0 | 0.6 |
| CO | | 20.1 | 19.6 | 9.0 |
| $CO_2$ | | 57.3 | 61.2 | 69.9 |
| $H_2O$ | | | | |
| Hydrocarbon Dist., wt. % | | | | |
| $C_1$ | | 5.8 | 6.7 | 8.5 |
| $C_2^o$ | | 2.4 | 4.4 | 6.2 |
| $C_2=$ | | 1.2 | 0.9 | 0.5 |
| $C_3^o$ | | 4.5 | 5.7 | 8.2 |
| $C_3=$ | | 3.8 | 2.7 | 1.3 |
| i-$C_4$ | | 6.6 | 7.7 | 8.2 |
| n-$C_4$ | | 5.2 | 5.5 | 7.2 |
| $C_4=$ | | 7.2 | 4.7 | 2.0 |
| i-$C_5$ | | 5.9 | 6.5 | 6.6 |
| n-$C_5$ | | 4.1 | 4.6 | 5.1 |
| $C_6+$ non-arom. | | 37.4 | 33.6 | 27.0 |
| Aromatics | | 15.9 | 17.0 | 19.2 |
| $C_1 + C_2$ in H.C., wt. % | | 8.2 | 11.1 | 15.2 |
| $C_3 + C_4$ in H.C., wt. % | | 28.5 | 27.3 | 26.9 |
| $C_5+$ in H.C., wt. % | | 63.3 | 61.6 | 57.9 |
| Aromatics in $C_5+$, wt. % | | 25.2 | 27.6 | 33.2 |
| Octane (R + O) of Liquid Product | | 91 | 89 | — |
| Boiling Range of Liquid Product (90% overhead) | | 354° F. | 371° F. | 353° F. |

Having thus generally described the method and sequence of steps of the present invention and specifically discussed examples in support thereof, it is to be understood that no undue restrictions are to be imposed by reason thereof except as defined by the following claims.

We claim:

1. In a process for converting syngas to carbon compounds comprising oxygenates and hydrocarbon products wherein syngas is contacted with an iron-containing Fischer-Tropsch catalyst at a temperature with the range of 400° to 600° F. and a pressure within the range of 1–1500 psig so as to achieve high conversion of said syngas to substantial amounts of $C_3+$ carbon compounds comprising no more than 20% methane plus ethane, and all or a portion of the product of said syngas conversion is passed in contact with an acidic crystalline zeolite having a pore dimension greater than 5 Angstroms, a silica-to-alumina ratio of at least 12, and a constraint index within the range of 1–12 at a temperature of 530°–850° F., a pressure from about 1 atmosphere to about 800 psig, and at a space velocity of from about 0.2 to 30 WHSV so as to promote the formation of gasoline and distillate materials; the improvement which comprises increasing the rate of syngas conversion by maintaining a $H_2/CO$ ratio in the range of 0.5 to 1 and achieving an overall syngas conversion of greater than 60%.

2. The process of claim 1 wherein the acidic crystalline zeolite is ZSM5.

3. The process of claim 2 wherein water is charged with the syngas passed in contact with the CO reducing catalyst.

4. The process of claim 2 wherein conversion of the syngas produces $C_1$ to $C_{40}$ carbon compounds and the total product effluent of the Fischer-Tropsch operation is passed in contact with the zeolite catalyst.

5. The process of claim 2 wherein the conversion of syngas is accomplished in more than one CO reduction zone and at least one zone employs the CO reduction catalyst suspended in a liquid medium.

6. The process of claim 2 wherein the products of Fischer-Tropsch synthesis comprise hydrocarbon and oxygenates which are separated and separately processed over said special zeolite catalyst to produce gasoline and distillate product.

7. The process of claim 2 wherein the high conversion of the syngas feed produces less than 20% methane plus ethane, the yield of $C_3$ plus products is at least 80% and the yield of $C_5$ plus products is at least 45%.

8. The process of claim 2 wherein the $H_2/CO$ ratio of the syngas is within the range of 0.6 to 0.8.

9. The process of claim 2 wherein the conversion of syngas by said Fischer-Tropsch catalyst is accomplished in an elongated reaction zone comprising suspended catalyst particles in a liquid medium.

10. The process of claim 2 wherein conversion of syngas by said Fischer-Tropsch catalyst is accomplished in the presence of a fixed bed of catalyst particles retained in an elongated tubular reaction zone surrounded by a heat exchange medium.

11. The process of claim 2 wherein the conversion of the low ratio syngas is effected in at least two separate catalyst zones in series and the removal of formed $CO_2$ is accomplished between catalyst zones.

* * * * *

UNITED STATES PATENT AND TRADEMARK OFFICE
CERTIFICATE OF CORRECTION

PATENT NO. : 4,279,830
DATED : July 21, 1981
INVENTOR(S) : Werner O. Haag and Tracy J. Huang It is certified that error appears in the above-identified patent and that said Letters Patent are hereby corrected as shown below:

| | |
|---|---|
| Col. 8, line 46 | Change "importnt" to --important-- |
| Col. 13, line 10 | Change "generlly" to --generally-- |
| Col. 13, line 20 | Change "generlly" to --generally-- |
| Col. 15, line 41 | Change "$C_250$" to --$C_2=$-- |
| Col. 15, line 43 | Change "$C_350$" to --$C_3=$-- |
| Col. 15, line 45 | Change "$C_450$" to --$C_4=$-- |
| Col. 17, line 22 | Change "$C_450$" to --$C_4=$-- |
| Col. 17, line 24 | Change "$C_630$" to --$C_6+$-- |
| Col. 20, line 29 | Insert the figures under Columns in Table 8 "1.7   1.2   1.0" |
| Col. 22, line 2 | Delete the word "special" |

Signed and Sealed this

Nineteenth Day of January 1982

[SEAL]

Attest:

Attesting Officer

GERALD J. MOSSINGHOFF

Commissioner of Patents and Trademarks